(12) United States Patent
Oh et al.

(10) Patent No.: US 10,736,401 B2
(45) Date of Patent: Aug. 11, 2020

(54) METHOD FOR PROVIDING A PREDETERMINED BEAUTY TREATMENT

(71) Applicant: Voesh Corporation, Plainview, NY (US)

(72) Inventors: Seunghee Oh, Roslyn Heights, NY (US); Joseph Choi, Roslyn Heights, NY (US)

(73) Assignee: VOESH CORPORATION, South Plainfield, NJ (US)

( * ) Notice: Subject to any disclaimer, the term of this patent is extended or adjusted under 35 U.S.C. 154(b) by 521 days.

(21) Appl. No.: 15/729,113

(22) Filed: Oct. 10, 2017

(65) Prior Publication Data

US 2018/0027945 A1 Feb. 1, 2018

Related U.S. Application Data

(63) Continuation of application No. 15/099,315, filed on Apr. 14, 2016.
(Continued)

(51) Int. Cl.
*A45D 37/00* (2006.01)
*B65D 75/58* (2006.01)
(Continued)

(52) U.S. Cl.
CPC .............. *A45D 37/00* (2013.01); *A61K 8/922* (2013.01); *A61K 8/9706* (2017.08); *A61K 8/9789* (2017.08); *A61K 8/9794* (2017.08); *A61Q 3/00* (2013.01); *A61Q 19/00* (2013.01); *B65D 75/5816* (2013.01); *B65D 77/02* (2013.01); *A45D 34/02* (2013.01);
(Continued)

(58) Field of Classification Search
CPC ................ A61Q 3/00; A61K 2800/884; A45D 2200/25; B65B 5/061; B65B 2220/16; B65B 2220/18
USPC ...... 53/449, 171; 206/223, 438, 570; 424/61
See application file for complete search history.

(56) References Cited

U.S. PATENT DOCUMENTS 2,635,788 A * 4/1953 Snyder et al. ......... B65D 75/48
222/107
2,663,450 A * 12/1953 Bourcart ................ A45D 40/00
220/522
(Continued)

FOREIGN PATENT DOCUMENTS

JP 02258506 A * 10/1990 ........... B65B 61/065
JP 2002000344 A * 1/2002 ......... A45D 2200/25
WO WO-2014031869 A1 * 2/2014 ............... B65B 5/08

*Primary Examiner* — Stephen F. Gerrity
(74) *Attorney, Agent, or Firm* — Tutunjian & Bitetto, P.C.

(57) ABSTRACT

The beauty or skin-care treatment may be a single use system for providing a manicure or pedicure treatment or other beauty or skin-care service. Each primary packaging that may be provided with the beauty or skin-care treatment may contain a beauty or skin-care product that may be used in providing the treatments. The beauty or skin-care treatment may include multiple primary packages in the form of single-serve packaging provided collectively as a set. The set may be housed in the secondary packaging and packaged together to form a multi-step treatment. The beauty or skin-care products contained in the single-serve packaging may be made of ingredients beneficial to the skin and may include products to aid in sanitizing, exfoliating, nourishing, hydrating and moisturizing the skin.

13 Claims, 9 Drawing Sheets

Related U.S. Application Data

(60) Provisional application No. 62/147,899, filed on Apr. 15, 2015.

(51) Int. Cl.

| | | |
|---|---|---|
| *A61Q 19/00* | (2006.01) | |
| *A61Q 3/00* | (2006.01) | |
| *A61K 8/92* | (2006.01) | |
| *B65D 77/02* | (2006.01) | |
| *A61K 8/9706* | (2017.01) | |
| *A61K 8/9789* | (2017.01) | |
| *A61K 8/9794* | (2017.01) | |
| *A45D 34/02* | (2006.01) | |
| *A45D 40/00* | (2006.01) | |

(52) U.S. Cl.
CPC .. *A45D 40/0087* (2013.01); *A45D 2200/1054* (2013.01); *A61K 2800/884* (2013.01); *B65D 2577/043* (2013.01)

(56) References Cited

U.S. PATENT DOCUMENTS

| | | | | |
|---|---|---|---|---|
| 4,706,693 A * | 11/1987 | Spector | ............ | A45D 40/26 132/320 |
| 6,656,484 B1 * | 12/2003 | Lube et al. | ............ | A45D 29/00 132/73 |
| 6,945,402 B1 * | 9/2005 | Gueret | ............ | B65D 81/3272 206/219 |
| 8,875,940 B2 * | 11/2014 | Danchisin et al. | .... | B65D 5/725 221/3 |
| 9,089,196 B2 * | 7/2015 | Mazurek | ............ | A45D 34/04 |
| 2002/0036155 A1 * | 3/2002 | Freeman et al. | ....... | A45D 33/00 206/581 |
| 2002/0114657 A1 * | 8/2002 | Gueret | ............ | A45D 34/04 401/130 |
| 2004/0195135 A1 * | 10/2004 | Seamon | ............ | A45C 13/02 206/459.1 |
| 2007/0062956 A1 * | 3/2007 | Roher et al. | ............ | B65D 5/02 220/520 |
| 2007/0178060 A1 * | 8/2007 | Xiu | ............ | A61K 8/9706 424/74 |
| 2008/0105328 A1 * | 5/2008 | Desmond | ............ | A45F 5/00 141/2 |
| 2009/0113847 A1 * | 5/2009 | Monti | ............ | B65B 5/106 53/153 |
| 2009/0181133 A1 * | 7/2009 | Luber et al. | ............ | B65D 77/06 426/108 |
| 2009/0188826 A1 * | 7/2009 | Porteous et al. | ...... | B65D 5/4216 206/459.5 |
| 2010/0124561 A1 * | 5/2010 | Studin | ............ | A61K 8/02 424/401 |
| 2010/0274205 A1 * | 10/2010 | Morelli et al. | ......... | A61B 50/30 604/290 |
| 2010/0314267 A1 * | 12/2010 | Green et al. | ............ | A61L 2/22 206/232 |
| 2011/0117225 A1 * | 5/2011 | Wei et al. | ............ | A61Q 19/10 424/757 |
| 2012/0308166 A1 * | 12/2012 | Laske | ............ | B65D 75/5805 383/109 |
| 2014/0221500 A1 * | 8/2014 | Cheng | ............ | A61K 8/678 514/691 |
| 2015/0164215 A1 * | 6/2015 | Hohlbein et al. | .. | A46B 15/0085 206/581 |
| 2015/0274344 A1 * | 10/2015 | Sullivan et al. | ...... | B65D 75/326 53/492 |
| 2015/0298895 A1 * | 10/2015 | Corbett et al. | ........ | B65D 43/162 206/540 |
| 2015/0320173 A1 * | 11/2015 | Hau | ............ | A45D 29/04 132/200 |
| 2016/0256368 A1 * | 9/2016 | Santhanam et al. | ... | A45D 40/00 220/522 |

* cited by examiner

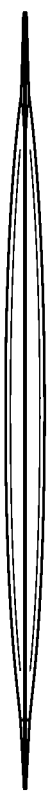
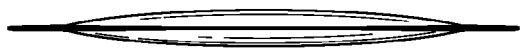
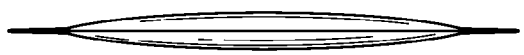
FIG. 4C   FIG. 4D
FIG. 4E
FIG. 4F
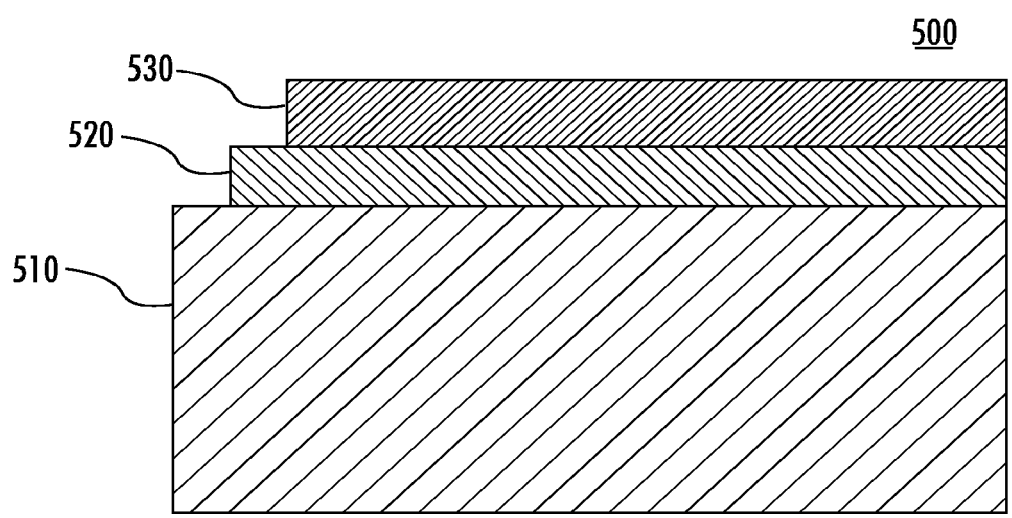
FIG. 5

METHOD FOR PROVIDING A PREDETERMINED BEAUTY TREATMENT

CROSS REFERENCE TO RELATED APPLICATIONS

This application is a Continuation of co-pending U.S. patent application Ser. No. 15/099,315 filed on Apr. 14, 2016 which claims the benefit of U.S. Provisional Application No. 62/147,899, filed Apr. 15, 2015, the entire contents of which is herein incorporated by reference.

FIELD OF DISCLOSURE

The present disclosure relates generally to a beauty product and more specifically to a method, apparatus, and system for beauty or skin-care services and products.

BACKGROUND OF THE DISCLOSURE

Skin care products are often used in providing manicure and pedicure, or other beauty or skin-care services for women as well as men. While there are myriad of skin care products available in the market like those that may be used in the various steps in a beauty or skin-care treatment, these skin-care products are often sold separately and in bulk or multi-use packaging.

This bulk packaging, often in five gallon containers, may be unsightly and take up limited space in a spa or salon, and at the same time may be unsuitable to provide display or point of sale advertisement of the service provided.

The multi-use packaging also affects how sanitary, effective, or pleasing to the senses the skin-care product may be. In bulk packaging, the skin-care or beauty product may become contaminated from repeated contact with technicians or users and the environment as a result of being accessed many times as a technician accesses the contents of the multi-use packaging on a repeated basis. Beauty and skin-care products stored in multi-use packaging may also suffer from a reduced shelf-life due to repeated exposure to the environment each time a technician accesses the contents of the multi-use packaging. The beauty or skin-care product may accordingly also suffer from reduced quality and diminished aroma and may become stale.

The application of beauty and skin-care products from multi-use packaging may also be imprecise, as there may not be a way to administer a consistent application of product to each user. Each technician may have his or her own idea of how much beauty or skin-care product is appropriate for an application for each given user. This may make it difficult for a service provider to provide a standardized and consistent beauty or skin-care treatment to its customer.

Bulk or multi-service packaging may also make it more difficult for a service provider to keep track of its inventory when it may not be sure how many servings may be found in the multi-use packaging. A service provider may also have to make large initial investments in bulk multi-use packaging of beauty and skin-care product, and thus, may also be hesitant to make similar investments to try new products and service that may also require upfront costs.

There exists an unfulfilled need for an improved beauty or skin-care treatment that allows delivery of a pre-measured amounts of beauty or skin-care product contained in single-serve packaging and collected together as a multi-step treatment that may overcome these and other concerns

SUMMARY OF THE DISCLOSURE

In accordance with the disclosed subject matter, a single use system for providing a manicure or pedicure treatment, or other beauty or skin-care treatment, is provided.

According to an aspect of this disclosure, a system for beauty or skin-care treatments is provided, comprising a plurality of skin-care products, wherein the skin-care products may include at least one of a scrub and a lotion. The plurality of skin-care products may be provided in single-serve packages and may share a common fragrance. The common fragrance may also provide aromatherapy and each of the single-serve packages may indicate the common fragrance and each single-serve package may comprise a step in a beauty or skin-care treatment. The single-serve packages may be disposed collectively in an outer package.

According to another aspect of the system for beauty or skin-care treatments, the plurality of skin-care products may further comprise at least one of a mask and a soak and may further comprise at least one of a callus remover and a moisturizer. The common fragrance may be derived from an aromatic ingredient and the common fragrance may also be derived from the group consisting of green tea, lemon, lavender, seaweed, grapefruit, olive oil, tangerine, cucumber, milk and honey, and aloe. The aromatic ingredient may also be a natural extract.

According to another aspect of the system for beauty or skin-care treatments, the single-serve package may comprise a wider width at a bottom end and a narrower width at a top end and may also comprise a silhouette of a bottle having a neck portion and a body portion. The single-serve package may comprise a notch on an edge to allow for opening of the single-serve package. The single-serve package may also be color-coded to indicate the common fragrance. According to another aspect of the system for beauty or skin-care treatments, the outer package may be substantially transparent and the outer package may be color-coded to indicate the common fragrance. The plurality of skin-care products may comprise a multi-step treatment for a pedicure or manicure treatment.

According to another aspect of the system for beauty or skin-care treatments, the single-serve packages may prevent contamination of the skin-care products and the single-serve packages may comprise ultraviolet protective material. The plurality of skin-care products may not be exposed to the environment until used and the single-serve packages may standardize the beauty or skin-care treatment, The outer packaging may further comprise a display to customers for the beauty or skin-care treatment and a service provider may provide new skin-care products and new beauty or skin-care treatments to spa customers without initial investment in a bulk supply of skin-care products and a service provider may inventory its the beauty or skin-care treatments.

According to yet another aspect of the disclosure, a beauty treatment is provided, comprising a plurality of skin-care products, wherein the skin-care products may include at least one of a scrub and a lotion, the plurality of skin-care products may be provided in single-serve packages and share a common characteristic; each of the single-serve packages may be coded based on the common characteristic; each single-serve packages may comprise a step in a multi-step beauty treatment; and the single-serve packages may be collected in an outer package.

According to another aspect of the beauty treatments, the common characteristic may be a fragrance and each of the single-serve packages may be color-coded based on the common characteristic.

According to yet another aspect of the disclosure, a beauty or skin-care treatment is provided, comprising a plurality of skin-care products, wherein the skin-care products may include at least one of a scrub, a soak, a mask, a lotion, and a moisturizer, the plurality of skin-care products may be provided in individual single-serve sachets and may share a common aromatic ingredient; each of the individual single-serve sachets may indicate the common aromatic ingredient; each individual single-serve sachet may comprise a step in a beauty or skin-care treatment; the individual single-serve sachets may each be disposed in a set for a single use; and wherein the plurality of skin-care products may comprise a multi-step treatment.

According to another aspect of the beauty or skin-care treatment, the beauty or skin-care treatment may comprise a pedicure or manicure treatment. The individual single-serve sachets may be coded to indicate the common aromatic ingredient.

According to yet another aspect of the disclosure, a method for providing a beauty treatment is provided, which may comprise: selecting a plurality of steps in a multi-step beauty treatment; selecting a fragrance for the multi-step beauty treatment; identifying a skin-care product having the selected fragrance for each of the plurality of steps selected; filling a plurality of single-serve sachets with the skin-care product for each of the plurality of steps selected; labeling each of the single-serve sachets with an associate step; and disposing the plurality of single-serve sachets as a single use set.

According to yet another aspect of the disclosure, the method may further comprise the step of color-coding the plurality of single-serve sachets with a color associated with the selected fragrance; the step of displaying the plurality of single-serve sachets in a partially transparent package; and the step of selecting a beauty treatment from among a manicure or a pedicure.

There has thus been outlined, rather broadly, the features of the disclosed subject matter in order that the detailed description thereof that follows may be better understood, and in order that the present contribution to the art may be better appreciated. There are, of course, additional features of the disclosed subject matter that will be described hereinafter and which will form the subject matter of the claims appended hereto.

In this respect, before explaining at least one embodiment of the disclosed subject matter in detail, it is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures for carrying out the several purposes of the disclosed subject matter. It is important, therefore, that the claims be regarded as including such equivalent constructions insofar as they do not depart from the spirit and scope of the disclosed subject matter.

These together with the other objects of the disclosed subject matter, along with the various features of novelty which characterize the disclosed subject matter, are pointed out with particularity in the claims annexed to and forming a part of this disclosure. For a better understanding of the disclosed subject matter, its operating advantages and the specific objects attained by its uses, reference should be had to the accompanying drawings and descriptive matter in which there are illustrated preferred embodiments of the disclosed subject matter.

BRIEF DESCRIPTION OF THE DRAWINGS

The accompanying drawings, which are included to provide a further understanding of the disclosure, are incorporated in and constitute a part of this specification, illustrate embodiments of the disclosure and together with the detailed description serve to explain the principles of the disclosure. No attempt is made to show structural details of the disclosure in more detail than may be necessary for a fundamental understanding of the disclosure and the various ways in which it may be practiced. In the drawings:

FIGS. 4A-4F are views from the front, rear, side, opposing side, top, and bottom respectively, of an embodiment of a beauty or skin-care product according to the principles of the disclosure of an inner packaging of a beauty product as illustrated in FIG. 3.

FIG. 5 is an example of a multi-layer material for an inner packaging of a beauty or skin-care product as illustrated in FIG. 3 in an embodiment according to the principles of the disclosure.

Figure 1A:
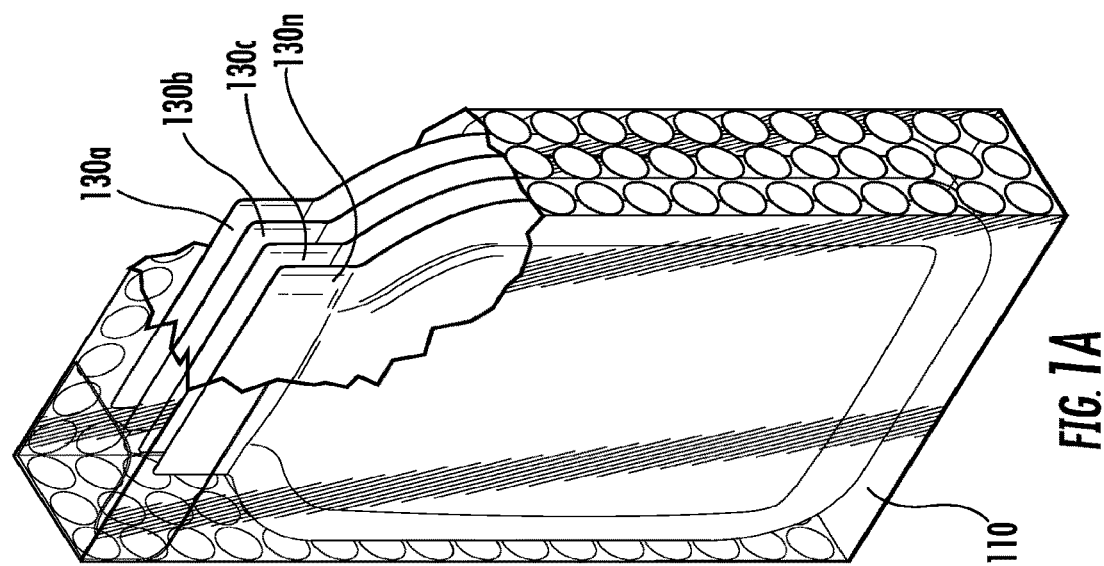
FIG. 1A is a perspective view, taken from FIG. 1 as indicated, having a cut-away to show a partial inner view of an embodiment of a beauty or skin-care product according to the principles of the disclosure.

The present disclosure is further described in the detailed description that follows.

DETAILED DESCRIPTION OF THE DRAWINGS

The disclosure and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components, processing, and techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure.

Accordingly, the examples and embodiments herein should not be construed as limiting the scope of the disclosure. Moreover, it is noted that like reference numerals represent similar parts throughout the several views of the drawings.

The terms "including", "comprising" and variations thereof, as used in this disclosure, mean "including, but not limited to", unless expressly specified otherwise.

The terms "a", "an", and "the", as used in this disclosure, means "one or more", unless expressly specified otherwise.

Although process steps, method steps, or the like, may be described in a sequential order, such processes and methods may be configured to work in alternate orders. In other words, any sequence or order of steps that may be described does not necessarily indicate a requirement that the steps be performed in that order. The steps of the processes or methods described herein may be performed in any order practical. Further, some steps may be performed simultaneously.

When a single layer or article is described herein, it will be readily apparent that more than one layer or article may be used in place of a single layer or article. The functionality or the features of a layer or article may be alternatively embodied by one or more other layers or articles which are not explicitly described as having such functionality or features.

Figure 1:
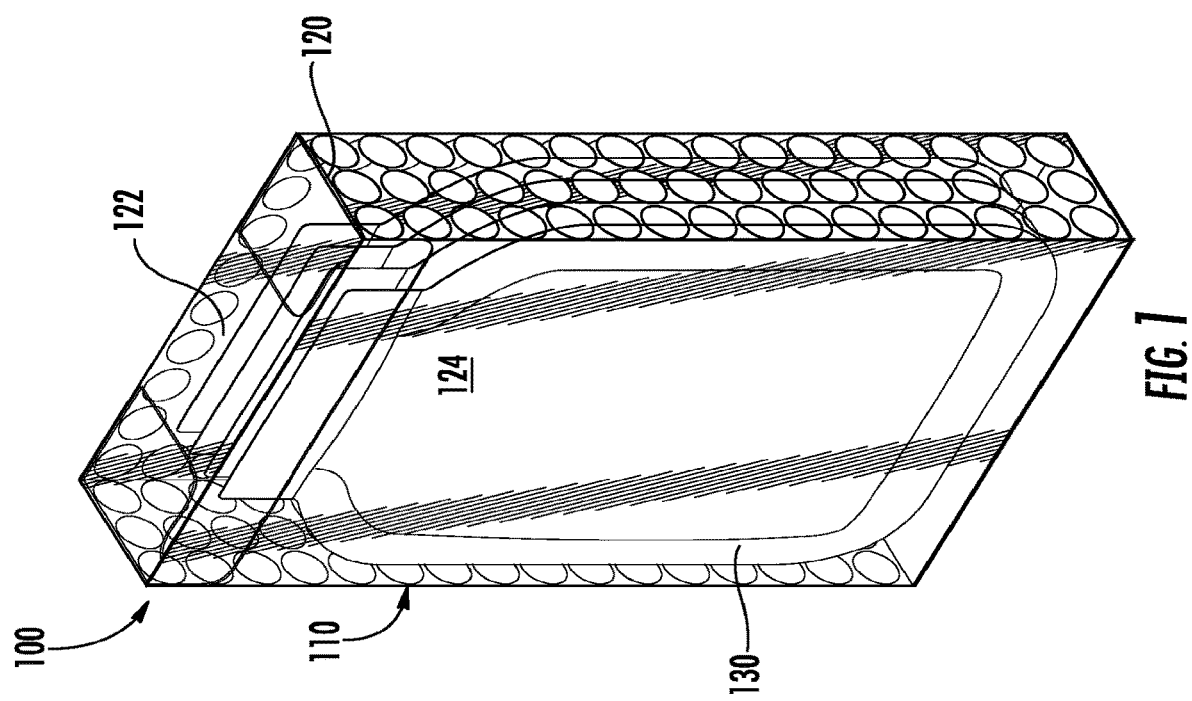
FIG. 1 is a perspective view of an embodiment according to the principles of the disclosure of an outer packaging of a beauty or skin-care product.
Figure 2A:
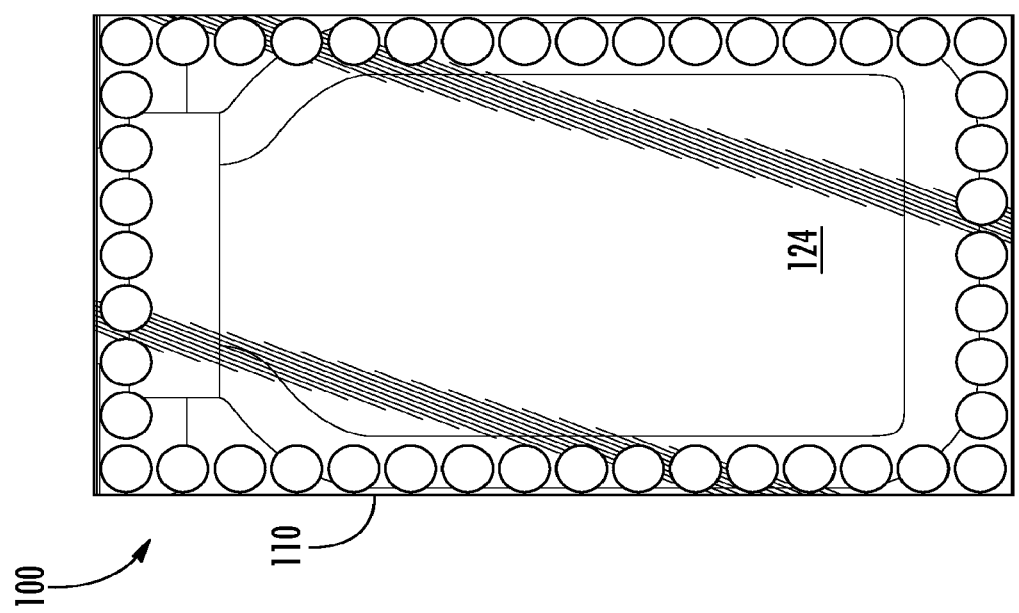
FIGS. 2A-2F are views from the front, rear, side, opposing side, top, and bottom respectively, of an embodiment of a beauty or skin-care product according to the principles of the disclosure of an outer packaging of a beauty product as illustrated in FIG. 1.
Figure 2B:
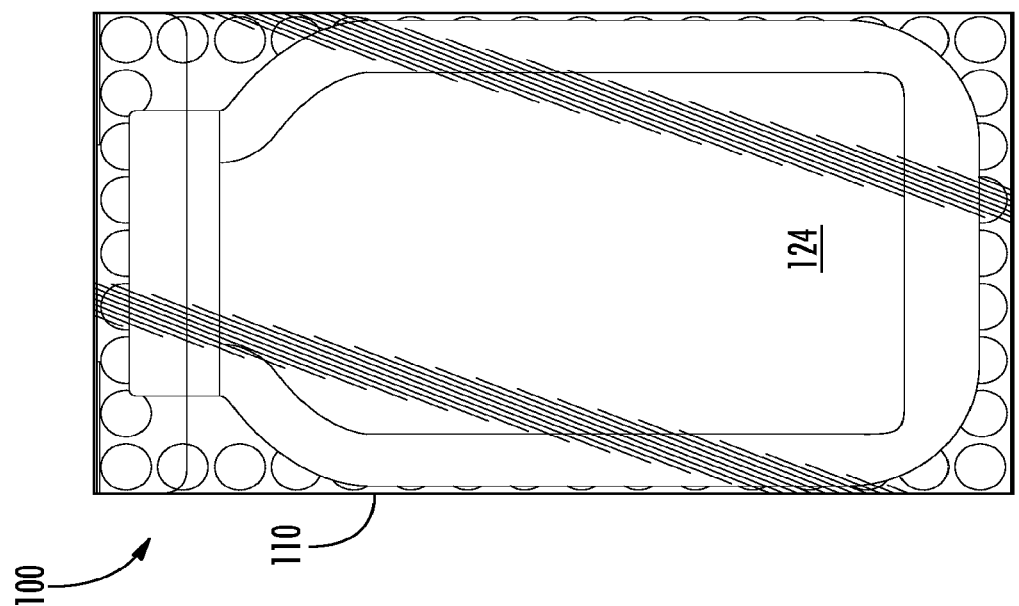
Figure 2E:
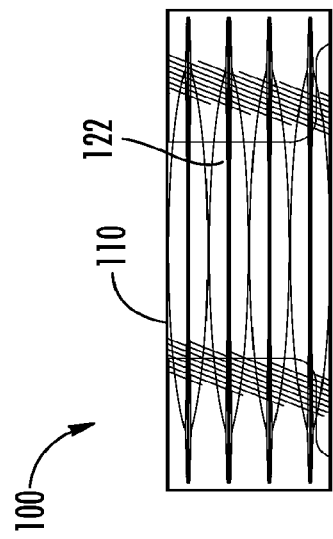
Figure 2F:
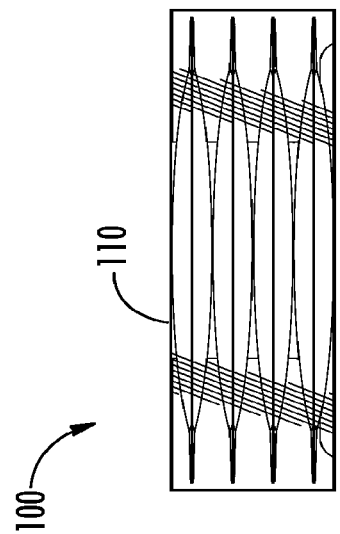
Figure 2D:
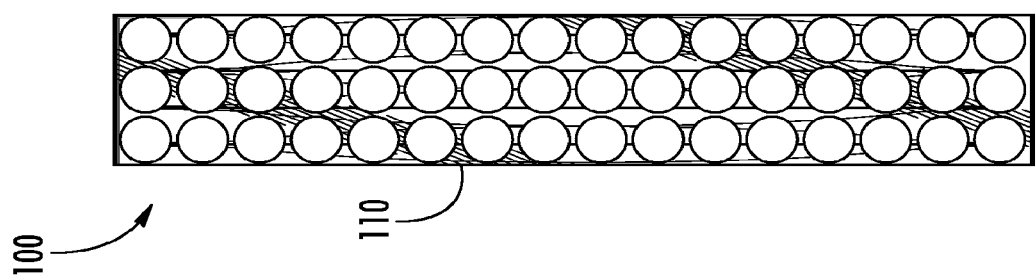
Figure 2C:
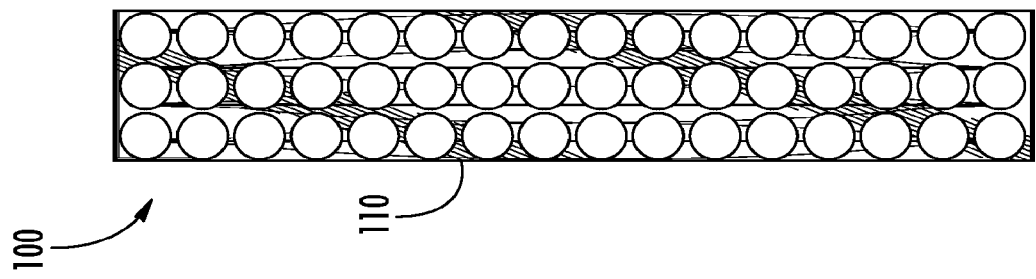
Figure 3:
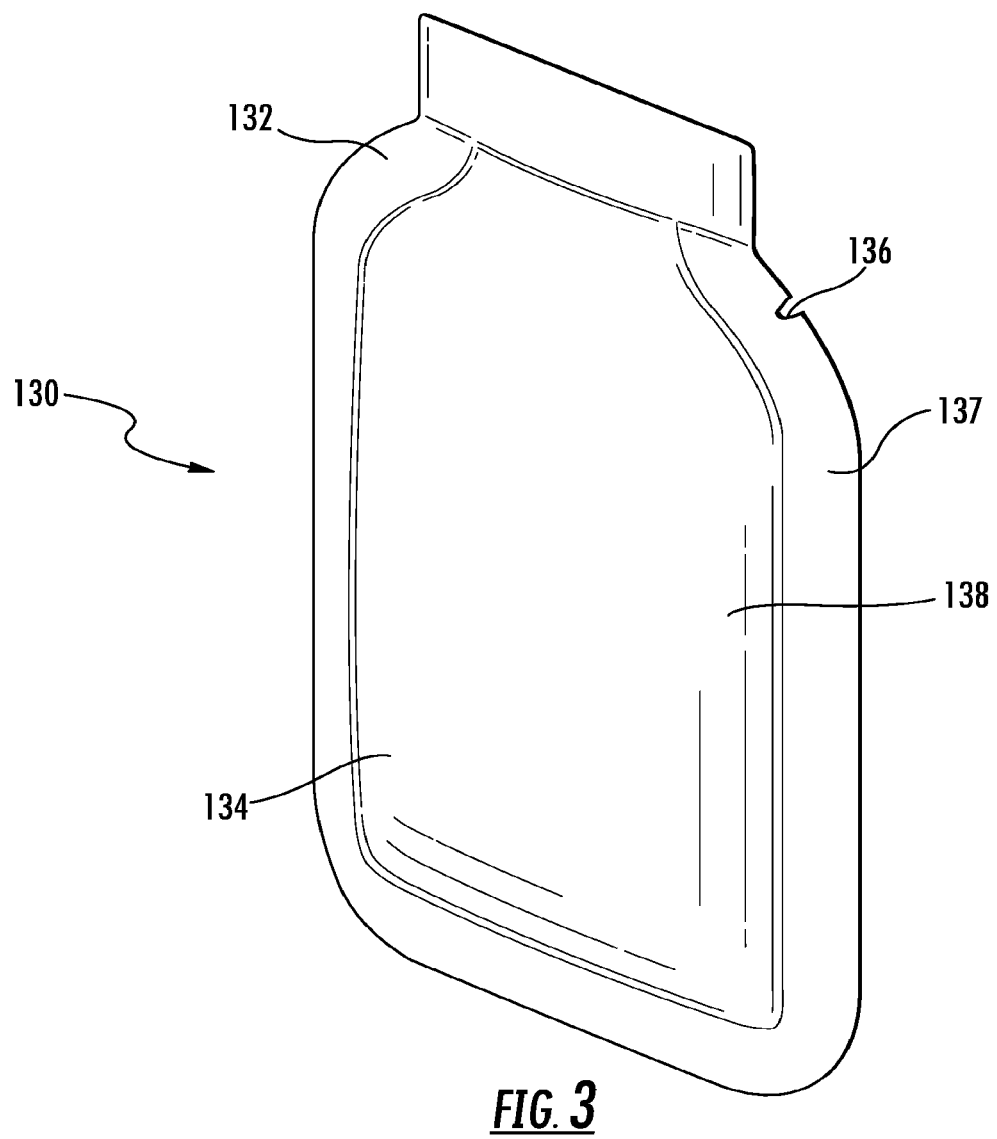
FIG. 3 is a perspective view of an embodiment of a beauty or skin-care product according to the principles of the disclosure of an inner packaging of a beauty product.
Figure 4B:
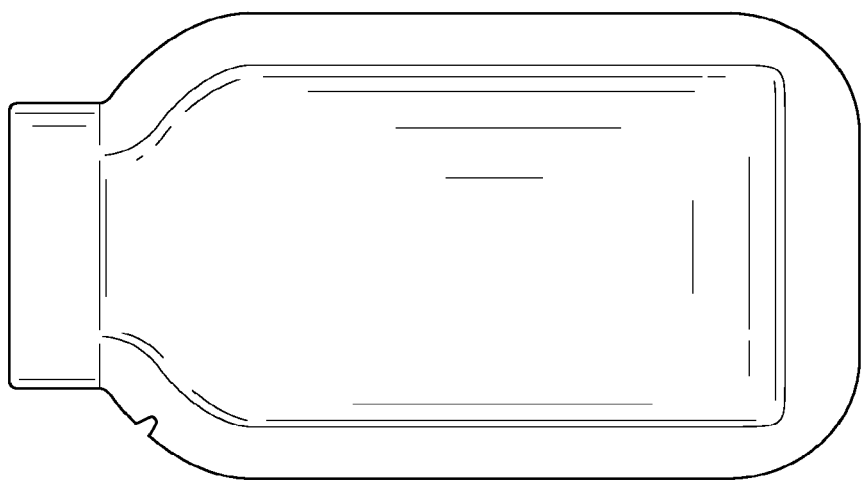
Figure 4A:
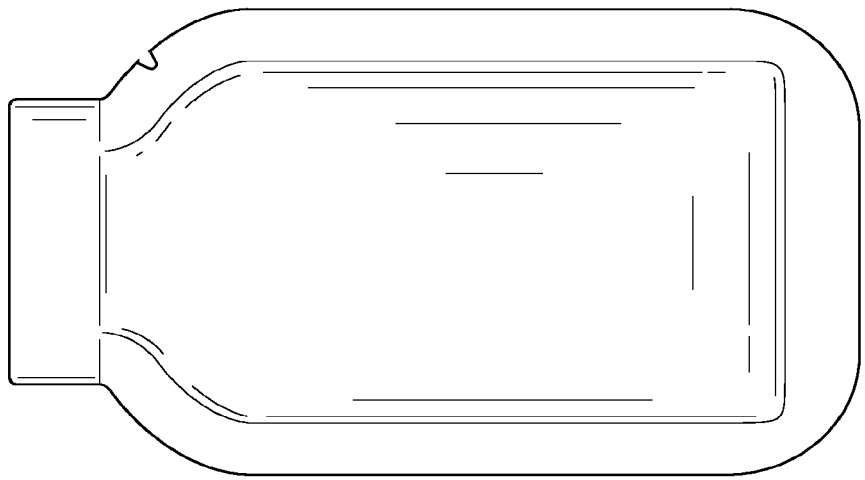

FIG. 1 shows an example of a beauty or skin-care product or treatment 100 according to the principles of the disclosure. The beauty or skin-care product or treatment 100 may be housed in a container packaging 110 which may be in the form of a rectangular box, as shown in FIG. 1, or of other suitable shape and size to contain the beauty treatment 100. Container packaging, or secondary packaging, 110, as it may also be referred to herein and discussed further below, may be used to house various primary packaging 130 that may directly house beauty or skin-care products.

The secondary packaging 110 may be formed of plastic, paper, cardboard or other suitable material known in the art and may have an opening 120 at least one end to access primary packaging 130 within. The opening 120 may be configured for one-time opening or may be reclosable. Opening 120 may be reclosable by folding or tucking a flap 122 into a slot or through any other know means of opening and closing packaging known in the art. The secondary packaging 110 may also be accessed by tearing apart an opening 120. The secondary packaging 110 may serve to display the beauty or skin-care treatment 100 service to potential customers by having a complete treatment on display. The secondary packaging 110 may also include a tab or flap for hanging the beauty or skin-care treatment 100 for point of sale display.

The secondary packaging 110 may be fully or partially transparent or completely opaque depending on design choices on its outer surface 124. The secondary packaging 110 may further include labels, lettering, or be coded to identify the beauty or skin-care treatment 100, or provide additional information about the beauty or skin-care treatment. The coding may be a color coding, or a common insignia, graphic or marking to indicate a common element shared with by the primary packaging 130 or the contents of the primary packaging.

The secondary packaging 110 may hold at least one package 130a, 130b, 130c . . . 130n, containing a beauty or skin-care product such as a lotion, a mask, a scrub, a soak, or the like, which may be referred to as primary packaging. While the primary packages 130 containing a beauty or skin-care product may be hidden from view by an opaque secondary packaging 110, it may also be visible or partially visible through a fully or partially transparent secondary packaging 110. FIG. 1A is a cut-away view of the secondary packaging 110 showing the primary packages 130a, 130b, 130c . . . 130n contained within secondary packaging 110.

Tertiary packaging (not shown) may also be used for point of sale display and may also may further include labels, lettering, or be similarly coded to identify the beauty treatment 100 or to indicate a common element shared with by the primary packaging 130 or the contents of the primary packaging.

FIGS. 3 and 4A-4F show an example of the primary packages 130 which may contain various beauty or skin-care products. The primary package 130 may be machine filled with product and sealed, which may block any outside air or contaminants from being exposed to the product. The contents of the primary packaging may thus be protected from becoming stale, contaminated, or losing quality or effectiveness due to exposure to the environment.

The primary packages 130a, 130b, 130c . . . 130n(FIG. 1A) may be formed in any shaped desired such that at least one primary package may fit within the secondary packaging 110. In an embodiment, the primary packages 130a, 130b, 130c . . . 130n may be formed to have a wider width near its lower half and a narrower width near its top end. In an embodiment illustrated in FIG. 3, the primary packaging 130 may be formed in a bottle shape or bottle silhouette shape. The primary packaging may have a top portion 132 and a bottom portion 134. The primary packaging may have a top portion which may resemble the neck of the bottle and may have a bottom portion that may resemble the body of a bottle. In an embodiment, the primary package 130 may be designed to be self-standing if a user rested it on a surface during a treatment.

The primary packaging 130 may include a slight groove, slice, perforation, or notch 136 on a perimeter 137 edge which may be used to facilitate opening the package 130 and accessing its contents by a user. In an embodiment, the notch 136 may be on the top portion 132. The slight groove, slice, perforation or notch 136 may partially penetrate a thin or substantially flat perimeter 137, and may allow a user to more easily unseal an inner, thicker pouch portion 138 of the primary packaging 130. Providing a sealed primary package 130 having a notch 136 on an edge to facilitate access to its single-service contents for a single use, may allow for easier handling of a primary packaging 130 while preventing leaks during storage and transportation.

In the embodiment illustrated in FIGS. 3 and 4A-4F, the secondary packaging 130 may be in the form of a pouch or a packet, or may be a sachet in the form sometimes used in the beauty and skin-care industry for single service or sample sized provision of beauty or skin-care product. The sachets may be individual sized and may be disposable and meant for one-time use. The single-serve primary packages 130 may be filled with measured amounts of beauty or skin-care products sufficient for a single application. A single-serve sachet 130 may allow a user or technician to apply a consistent amount of product for each step and provide a standardized beauty or skin-care treatment for each user. Also a service provider may more easily track its inventory if each beauty or skin-care treatment 100 is a single treatment.

In an embodiment, the primary package 110, may be formed of plastic polymers, such as, e.g., polyester (PET), polypropylene (PP), poly vinyl chloride (PVC), polystyrene (PS), poly lactic acid (PLA), polycarbonate (PC) or the like. Alternatively, (or additionally), the sachet 130 may include a material that can be a blend of the plastic polymers. FIG. 5 illustrates an example of a multi-layer material 500 to form a sachet 130. In an embodiment, the sachet 130 may include three layered UV protective and light resistant materials 510, 520, and 530 to allow for longer shelf life of material(s) inside the sachet 130. The multi-layer material 500 may be formed from methods that may include lamination, vacuum-metalization, vapour-deposited coat, an extrusion, and/or calendered plastic to extrude the UV protective material. The extrusion and/or calendered process may include, for example, blown film extrusion, sheet/film extrusion, tubing extrusion, overjacking extrusion, coextrusion, extrusion coating, film casting, calendering, and the like.

The beauty or skin-care treatment 100 may be a single use system for providing a manicure or pedicure treatment or other beauty or skin-care treatment. Each primary packaging 130 that may be provided with the beauty or skin-care treatment 100 may contain a beauty or skin-care product that may be used to provide manicure, pedicure, or any other beauty or skin-care treatment. The beauty or skin-care treatment 100 may include multiple primary packages 130 in the form of single-serve packaging 130 provided collectively as a set. The set may be housed in the secondary packaging 110 and packaged together to form a manicure or pedicure spa treatment 100. The beauty or skin-care products contained in the single-serve packaging 130 may be made of ingredients beneficial to the skin and may include products to aid in sanitizing, exfoliating, nourishing, hydrating and moisturizing the skin.

In an embodiment, the beauty or skin-care treatment 100 may be provided for use in pedicure or manicure treatments, where the appropriate beauty or skin-care products are provided for whichever type of treatment is indicated. For example, different types of beauty or skin-care products may be more appropriate for a hand treatment than for a foot treatment, although some beauty or skin-care products may be used with many beauty or skin-care treatments commonly used in the industry. The primary packaging 130 may contain a single-serving of an indicated beauty or skin-care product to allow a user or technician to apply the beauty or skin-care product as a step as part of treatment.

Because the primary packaging 130 may contain a pre-measured amount of an indicated beauty or skin-care product, a standardized application of product may be possible. Also a service provider may be able to account for the number of treatments in its inventory or the precise number of additional treatments it may choose to buy.

Examples of the types of beauty or skin-care products contemplated may include scrubs, soaks, masks, lotions, callus removers and moisturizers. This list is non-exhaustive and any beauty or skin-care products known in the art for use in manicure or pedicure treatments, or applicable beauty or skin-care treatment of the types provided in spas, salon, or administered at home, are contemplated. The beauty or skin-care treatment 100 may also be applied to any other spa, salon, or skin treatments, such as facials, massages, waxings, etc. Other beauty or skin-care products may include peels, waxes, or gels. This disclosure is not limited with regard to whether a treatment is predominately beauty related or skin-care related and it is contemplated that there may be substantial overlap between each.

Figure 6:
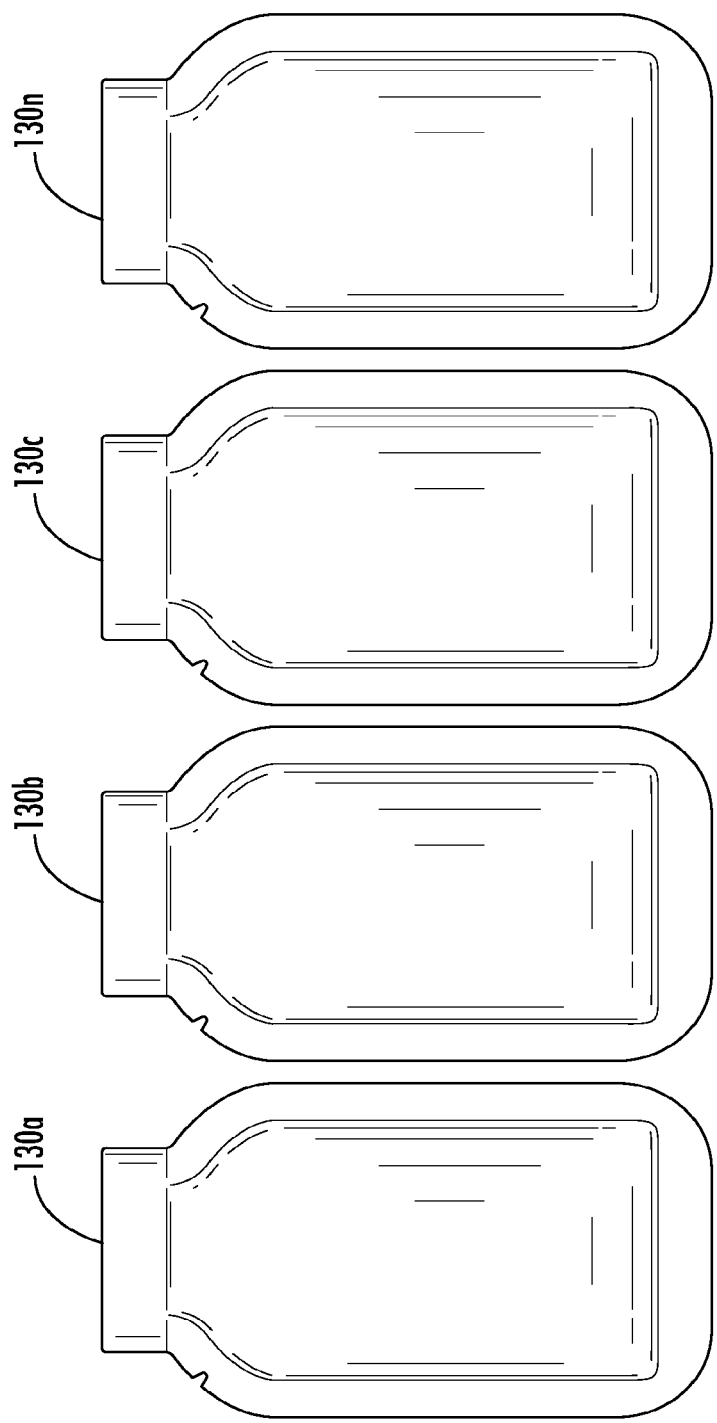
FIG. 6 is a front plan view of a set 1 through nth inner packages as illustrated in FIG. 3 in an embodiment according to the principles of the disclosure.

In an embodiment, the beauty or skin-care treatment 100 may include at least two steps in the treatment, and accordingly may comprise at least two primary packages 130 of single-serve beauty or skin-care products. In various embodiments, the beauty treatment 100 may be a "two step in one" treatment, a "three step in one" treatment, a "four step in one" treatment, a "five step in one" treatment, a "six step in one" treatment through a "nth step in one" treatment, as illustrated in FIG. 6.

In an embodiment, two included steps may be a scrub and a lotion. In another embodiment, additional steps may be a mask and soak. Further additional steps, in yet other embodiments may include callus removers and moisturizers. The number and order of the primary packages 130 and the steps is not intended to be limiting and the beauty or skin-care treatment 100 primary packages 130 may be assembled inside the secondary package 110 in any order.

For purposes of this disclosure, the term scrub may also include various known exfoliators and abrasives, and may act on the skin either physically or mechanically or provide a chemical scrub. Types of scrubs may include salts, sugars, silica, microbeads baking soda, steric acid, and various other scrubs known in the art.

For purposes of this disclosure, the term soak may also include various known baths. Types of soaks may include salts, bubble baths, confetti soaps, and various other soaks known in the art.

For purposes of this disclosure, the term lotion may also include various known moisturizers, creams, butters, emulsions and essences. Types of lotions may include massaging and hydrating lotions, and various other lotions known in the art.

Embodiments of sets of steps for a 3 in 1 beauty or skin-care treatment 100 may include three sachets 130, for example, including one each of a scrub, a mask, and a lotion or including three sachets 130, one each of a soak, a scrub, and a lotion. Embodiment of sets of steps for a 4 in 1 beauty or skin-care treatment 100 may include fours sachets 130, for example, including one each of a soak, a scrub, a mask, and a lotion. Embodiments of sets of steps for a 6 in 1 beauty or skin-care treatment 100 may include six sachets 130, for example, including a soak, a scrub, a mask, a lotion, a callus remover, and a moisturizer. Examples of sets of steps for a 7 in 1 beauty or skin-care treatment 100 may include seven sachets 130, for example, including a soak, a scrub, a mask, a lotion, a callus remover, a moisturizer, and a gel. The number of steps, the specific steps, and the order of the steps are not meant to be limiting, but are offered as examples of all in one, single serve, multi-step sets for a beauty or skin-care treatment 100.

In an embodiment, each of the steps for multi-step sets for a beauty treatment 100 may share one or more common characteristics. A common characteristic may be a scent, fragrance, perfume, or aroma. A common characteristic may also be a common essence or natural extract. Each sachet 130 may be coded to indicate the common characteristics. The coding may be a written description, a color coding, or an image or graphic on the primary packaging 130 to describe the common characteristic to a user or purchaser of the beauty or skin-care treatment 100. The coding may also be implemented on the secondary package 110, or also on any tertiary packaging. The secondary packaging 110 may also be at least partially transparent, which may make the coding on the primary packaging 100 visible to a user or purchaser. A common scent, fragrance, or aroma may also provide an aroma therapy treatment. The aroma therapy benefit may extend to each step in the beauty treatment 100 where a common characteristic may also be a common essence or natural extract that may provide additional health, beauty or skin-care benefits to a user of the beauty or skin-care treatment 100. A non-limiting and non-exhaustive list of examples of common or natural extracts that may be used in a beauty treatment 100 are green tea extract, lemon, lavender extract, seaweed extract, grapefruit, olive oil, tangerine, cucumber, milk and honey, and aloe.

Green Tea may reduce dryness in skin. Along with hydration, green tea may also be used to prevent premature aging of the skin, fight free radical damage and promote overall skin health.

Lemon is rich in fruit acids and may be a natural beautifying agent. Lemon contains enzymes which may help to cleanse the skin of dead cells and it antioxidants may help to flush away toxins and replenish the skin.

Lavender may provide benefits through antiseptic and anti-fungal properties which may help to reduce scarring and speed healing. Lavender may also boost the circulatory system, which may help increase the flow of oxygen and nutrients to the skin.

Seaweed extract may help nourish, protect, and increase circulation. Peppermint gives skin a cooling sensation for dry and hot days.

Vitamin C may protect skin cells and the skin's support structure. Vitamin C is an antioxidant that may slow the rate of free-radical damage which may cause skin dryness & wrinkles.

Olive oil provides antioxidants such as vitamin A and vitamin E that may help repair and renew skin damaged from environmental exposure.

Tangerine may have anti-fungal and antiseptic properties which may help prevent and treat skin infections and stretch marks.

Cucumber may have the same hydrogen level as one's skin which may sooth and soften skin and hide problem areas.

Milk and Honey may contain antioxidants that are beneficial to the skin and body.

Aloe may contain a plethora of antioxidants including beta carotene, vitamin C, and vitamin E that may help improve the skin's natural firmness and keep the skin fully replenished and hydrated.

A beauty or skin-care treatment is a service provided to customers often offered by spas, salons, and similar types of businesses. In embodiments of the beauty or skin-care treatment 100 disclosed herein, the beauty and skin-care products used in that treatment 100 may be purchased, stored, displayed, sold and used as a single-use good or product, allowing a service provided a new way to inventory the number of services or treatments it has or is able to provide simply by accounting for the number of beauty or skin-care treatments 100.

Figure 7:
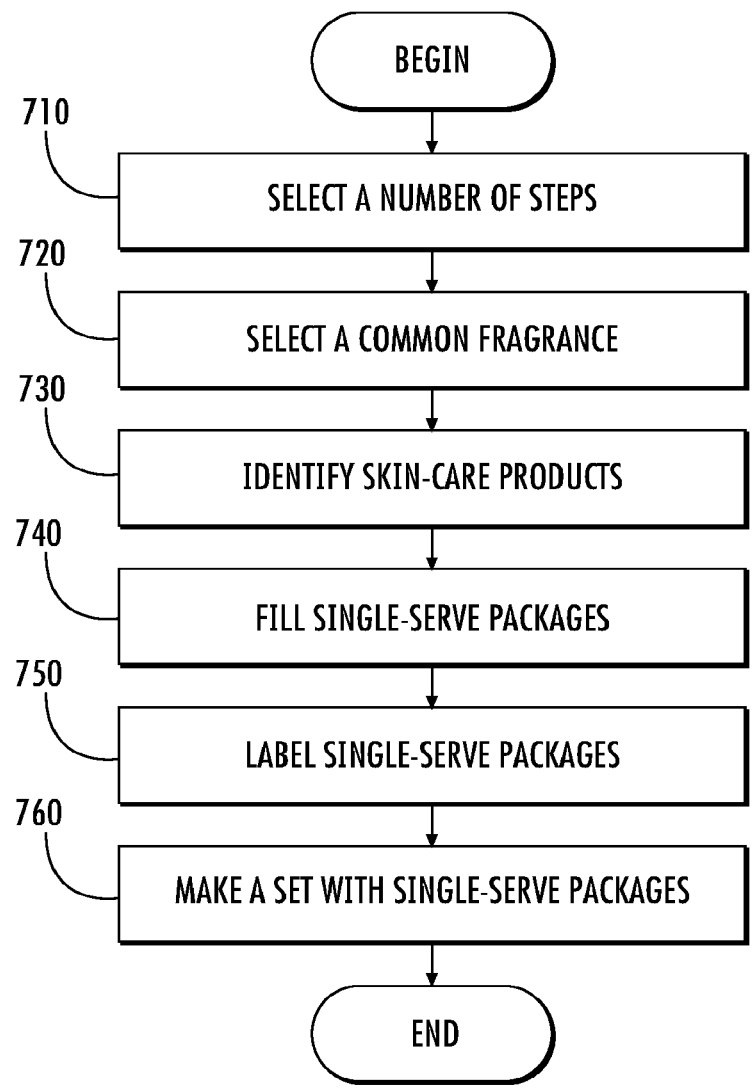
FIG. 7 shows an example of a method for making the beauty or skin-care product, according to the principles of the disclosure.

FIG. 7 shows an example of a method for providing a beauty or skin-care treatment 100. The method may include selecting a plurality of steps in a multi-step pedicure or manicure treatment 100 (710), and selecting a fragrance for the multi-step pedicure or manicure treatment 100 (720). The method may also include identifying a skin-care product with the selected fragrance for each of the steps selected (730) and filling single-serve sachets 130 with the skin-care product for each of the steps selected (740). The single-serve sachets 130 may be labeled with its associate step (750) and the sachets 130 may be collected as a set 110 (760).

The method may also include color-coding the single-serve sachets 130 with a color associated with the selected fragrance and displaying the collection of single-serve sachets 110 in a partially transparent package 110.

Figure 8:
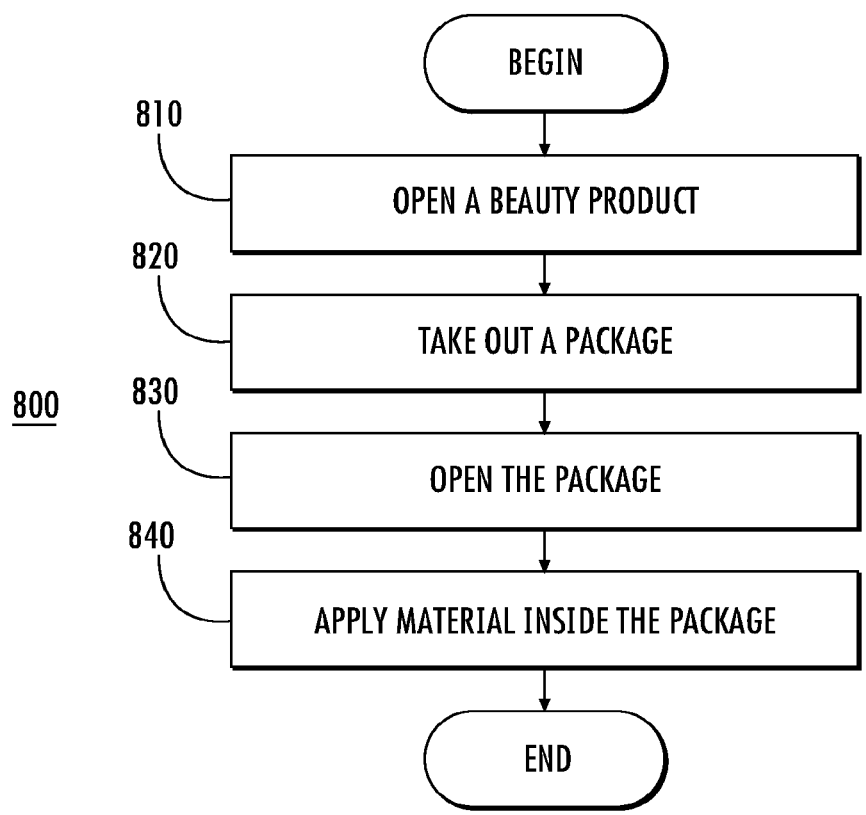
FIG. 8 shows an example of a method for using the beauty or skin-care product, according to the principles of the disclosure.

FIG. 8 shows an example of a method 800 for using a beauty or skin-care treatment 100. The method 800 may include: opening a beauty product wherein the beauty product may include at least one of the following packages: Scrub, Sugar Scrub, Mud Masque, Massage Lotion, and a Salt Soak (Step 810); taking the package out of the beauty product (Step 820); opening the package by ripping open a slight groove wherein the slight groove may be located in a top portion of the package (Step 830); and applying a material inside the package onto a user's skin (Step 840).

When a primary packaging 130 is used as a part of the beauty or skin-care treatment, it may be opened for the first and only time during a particular treatment. Thus, a service provider may avoid the application of product that may have been previously in contact with the environment, another technician or client's hands, or any other potential contaminants that may result from accessing product contained in multi-use or bulk packaging. The sealed and ultraviolet resistant primary packaging 130 may allow a service provider to provide beauty or skin-care products may be more fresh, effective, aromatic, and sanitary than if found in packaging had been previously opened or exposed to the environment.

While the disclosure has been described in terms of exemplary embodiments, those skilled in the art will recognize that the disclosure can be practiced with modifications in the spirit and scope of the appended claims. These examples are merely illustrative and are not meant to be an exhaustive list of all possible designs, embodiments, applications or modifications of the disclosure.

What is claimed is:

1. A method for providing a predetermined beauty treatment comprising:
    selecting a number of steps to be performed for the predetermined beauty treatment;
    selecting a common characteristic for each of the selected steps;
    manufacturing a separate packet of product to be used for each of the steps in the predetermined beauty treatment;
    labeling each separate packet with indicia representative of the selected step to which the packet corresponds;
    providing a packaging configured exclusively for the predetermined beauty treatment, said packaging being sized to only fit the manufactured separate packets of product for each of the steps to be used in the predetermined beauty treatment;
    inserting each of the manufactured packets into the provided packaging; and
    labeling the packaging with indicia representative of the predetermined beauty treatment.

2. The method according to claim 1, wherein said manufacturing a separate packet of product further comprises providing a notch on an edge of said separate packet to facilitate opening of said packet.

3. The method of claim 1, wherein said manufacturing a separate packet of product further comprises utilizing at least one layer having UV protective and light resistant properties.

4. The method of claim 1, wherein said common characteristic comprises one selected from a group consisting of a fragrance, a scent, a perfume, and an aroma.

5. The method of claim 1, wherein said common characteristic comprises a common essence or a natural extract.

6. The method of claim 1, wherein said predetermined beauty treatment is a pedicure or a manicure.

7. A method for implementing and providing a predetermined beauty treatment comprising:
- manufacturing separate packets of product to be used sequentially in the providing of the predetermined beauty treatment;
- labeling each manufactured separate packet with indicia representative of the sequential use to which the packet corresponds in the predetermined beauty treatment;
- providing a packaging configured exclusively for the predetermined beauty treatment, said packaging being sized to fit a predetermined number of said manufactured separate packets corresponding to the predetermined beauty treatment;
- inserting each of the manufactured separate packets for the predetermined beauty treatment into the provided packaging; and
- labeling the packaging with indicia representative of the predetermined beauty treatment.

8. The method of claim 7, wherein said manufacturing further comprises utilizing at least one layer having UV protective and light resistant properties.

9. The method of claim 8, wherein said manufacturing further comprises providing a notch on an edge of each separate packet to facilitate opening of said packet.

10. The method of claim 7, wherein said manufacturing further comprises selecting a common characteristic for the manufactured separate packets based on the predetermined beauty treatment to be provided.

11. The method of claim 10, wherein said common characteristic comprises one selected from a group consisting of a fragrance, a scent, a perfume, and an aroma.

12. The method of claim 10, wherein said common characteristic comprises a common essence or a natural extract.

13. The method of claim 7, wherein said predetermined beauty treatment is a pedicure or a manicure.

* * * * *